(12) United States Patent
Larsen et al.

(10) Patent No.: US 8,894,611 B2
(45) Date of Patent: Nov. 25, 2014

(54) MEDICAL INJECTION DEVICE WITH TIME DELAY INDICATOR

(75) Inventors: Andre Larsen, Dragør (DK); Ole Christian Nielsen, Hillerød (DK); Salim Bouaidat, Copenhagen K. (DK); Jan Preuthun, Brønshøj (DK)

(73) Assignee: Novo Nordisk A/S, Bagsvaerd (DK)

( * ) Notice: Subject to any disclaimer, the term of this patent is extended or adjusted under 35 U.S.C. 154(b) by 778 days.

(21) Appl. No.: 13/061,257

(22) PCT Filed: Aug. 31, 2009

(86) PCT No.: PCT/EP2009/061191
§ 371 (c)(1),
(2), (4) Date: May 10, 2011

(87) PCT Pub. No.: WO2010/023303
PCT Pub. Date: Mar. 4, 2010

(65) Prior Publication Data
US 2011/0208125 A1    Aug. 25, 2011

Related U.S. Application Data

(60) Provisional application No. 61/093,755, filed on Sep. 3, 2008.

(30) Foreign Application Priority Data

Aug. 29, 2008   (EP) ..................... 08163283

(51) Int. Cl.
*A61M 37/00*   (2006.01)
*A61M 5/00*    (2006.01)
*A61M 5/24*    (2006.01)
*A61M 5/315*   (2006.01)
*A61M 5/31*    (2006.01)

(52) U.S. Cl.
CPC .............. *A61M 5/24* (2013.01); *A61M 5/31535* (2013.01); *A61M 2205/583* (2013.01); *A61M 2205/582* (2013.01); *A61M 5/3129* (2013.01); *A61M 5/3157* (2013.01); *A61M 2005/3143* (2013.01)
USPC ........................................ 604/111; 604/220

(58) Field of Classification Search
USPC ......... 604/140, 143, 146, 149, 187, 207–211, 604/218, 220–224, 228, 232–235, 111
See application file for complete search history.

(56) References Cited

U.S. PATENT DOCUMENTS 4,108,177 A  *  8/1978  Pistor .......................... 604/155
4,428,321 A       1/1984  Arens
(Continued)

FOREIGN PATENT DOCUMENTS

CN   1705495 A   12/2005
CN   1729028 A    2/2006
(Continued)

OTHER PUBLICATIONS

Trankler, Hans-Rolf, R. Oldenbourg, Verlag, Munchen, Wien, Taschenbuch Der Messtechnik, 1996.

*Primary Examiner* — Kevin C Sirmons
*Assistant Examiner* — William Carpenter
(74) *Attorney, Agent, or Firm* — Wesley A. Nicolas; Reza Green; Richard W. Bork (57) ABSTRACT

The present invention relates to an indicating device for use with medical injection devices for administering a drug into the body of a subject user wherein the indicating device is configured for indicating after administration that a dose of the drug actually has been administered and for maintaining this indication until lapse of a pre-defined time interval. The time delay indicator disclosed is based on a mechanical time delay device and includes a visual indicator that is controlled by the mechanical time delay device for signalling the status of the device during lapse of the pre-defined time interval.

13 Claims, 4 Drawing Sheets

(56) References Cited

U.S. PATENT DOCUMENTS

| | | | |
|---|---|---|---|
| 4,515,584 A | 5/1985 | Abe et al. | |
| 4,561,856 A * | 12/1985 | Cochran | 604/143 |
| 4,634,431 A | 1/1987 | Whitney et al. | |
| 4,744,786 A * | 5/1988 | Hooven | 604/143 |
| 4,776,842 A | 10/1988 | Franetzki et al. | |
| 4,812,724 A | 3/1989 | Langer et al. | |
| 4,828,551 A * | 5/1989 | Gertler et al. | 604/208 |
| 4,838,860 A | 6/1989 | Groshong et al. | |
| 4,898,578 A | 2/1990 | Rubalcaba, Jr. | |
| 5,084,021 A * | 1/1992 | Baldwin | 604/131 |
| 5,221,268 A | 6/1993 | Barton et al. | |
| 5,536,249 A | 7/1996 | Castellano et al. | |
| 5,593,390 A * | 1/1997 | Castellano et al. | 604/187 |
| 5,645,534 A | 7/1997 | Chanoch | |
| 5,662,612 A | 9/1997 | Niehoff | |
| 5,690,618 A | 11/1997 | Smith et al. | |
| 5,728,074 A * | 3/1998 | Castellano et al. | 604/207 |
| 5,755,692 A * | 5/1998 | Manicom | 604/152 |
| 5,998,989 A | 12/1999 | Lohberg | |
| 6,019,745 A | 2/2000 | Gray | |
| 6,027,491 A * | 2/2000 | Hiejima et al. | 604/891.1 |
| 6,090,070 A * | 7/2000 | Hager et al. | 604/131 |
| 6,126,642 A * | 10/2000 | Kriesel et al. | 604/207 |
| 6,236,624 B1 | 5/2001 | Kriesel et al. | |
| 6,248,090 B1 | 6/2001 | Jensen et al. | |
| 6,268,722 B1 | 7/2001 | Kogure et al. | |
| 6,464,663 B1 * | 10/2002 | Zinger | 604/82 |
| 6,547,755 B1 | 4/2003 | Lippe et al. | |
| 6,620,133 B1 * | 9/2003 | Steck | 604/131 |
| 7,008,399 B2 | 3/2006 | Larsen et al. | |
| 7,139,226 B2 | 11/2006 | Haas et al. | |
| 7,244,252 B2 | 7/2007 | Berndt | |
| 7,294,379 B2 | 11/2007 | Ko et al. | |
| 7,427,275 B2 | 9/2008 | DeRuntz et al. | |
| 7,963,692 B2 | 6/2011 | Lynn | |
| 8,409,138 B2 * | 4/2013 | James et al. | 604/110 |
| 8,556,847 B2 * | 10/2013 | Kohlbrenner et al. | 604/67 |
| 2003/0114800 A1 | 6/2003 | Veasey et al. | |
| 2005/0222539 A1 | 10/2005 | Gonzales et al. | |
| 2005/0273055 A1 * | 12/2005 | Harrison et al. | 604/136 |
| 2006/0235086 A1 | 10/2006 | Maskaly et al. | |
| 2007/0293822 A1 | 12/2007 | Crawford et al. | |
| 2009/0076458 A1 | 3/2009 | Nielsen et al. | |
| 2012/0103329 A1 * | 5/2012 | Smith | 128/203.12 |
| 2012/0109071 A1 | 5/2012 | Larsen et al. | |

FOREIGN PATENT DOCUMENTS

| | | |
|---|---|---|
| DE | 10021313 A1 | 11/2001 |
| DE | 10201875 C1 | 5/2003 |
| DE | 10236669 A1 | 2/2004 |
| DK | 200100240 U3 | 11/2001 |
| EP | 0362484 A2 | 4/1990 |
| EP | 387854 | 9/1990 |
| EP | 688572 | 12/1995 |
| EP | 40778961 | 1/1997 |
| EP | 1074273 | 2/2001 |
| EP | 1095668 A1 | 5/2001 |
| EP | 1361908 | 11/2003 |
| EP | 1467785 | 10/2004 |
| EP | 1804864 | 7/2007 |
| FR | 2740345 | 4/1997 |
| FR | 2990866 A1 * | 11/2013 |
| JP | 04004393 A | 1/1992 |
| JP | 11134581 A | 5/1999 |
| JP | 2000-506030 | 5/2000 |
| JP | 2001-517496 A | 10/2001 |
| JP | 2002-504397 A | 2/2002 |
| JP | 2004-516110 A | 6/2004 |
| JP | 2005-511252 A | 4/2005 |
| JP | 2005270579 A | 10/2005 |
| RU | 2140794 C1 | 11/1999 |
| SU | 1528330 A3 | 12/1989 |
| WO | 90/09202 | 8/1990 |
| WO | 96/04593 | 2/1996 |
| WO | 9730742 | 8/1997 |
| WO | 9915214 | 4/1999 |
| WO | 99/43283 | 9/1999 |
| WO | 00/20056 A1 | 4/2000 |
| WO | 0126710 | 4/2001 |
| WO | 02/056822 | 7/2002 |
| WO | 02064196 | 8/2002 |
| WO | 03/051429 | 6/2003 |
| WO | 9733638 | 9/2003 |
| WO | 03/092575 | 11/2003 |
| WO | 2004/010231 | 1/2004 |
| WO | 2004/062717 A1 | 7/2004 |
| WO | 2006/045524 A1 | 5/2006 |
| WO | 2007/134067 | 11/2007 |
| WO | 2008/067143 | 6/2008 |
| WO | WO 2008112472 A2 * | 9/2008 |
| WO | 2010/023303 | 3/2010 |

* cited by examiner

MEDICAL INJECTION DEVICE WITH TIME DELAY INDICATOR

CROSS-REFERENCE TO RELATED APPLICATIONS

This application is a 35 U.S.C. §371 national stage application of International Patent Application PCT/EP2009/061191 (published as WO 2010/023303), filed Aug. 31, 2009, which claimed priority of European Patent Application 08163283.8, filed Aug. 29, 2008; this application further claims priority under 35 U.S.C. §119 of U.S. Provisional Application 61/093,755, filed Sep. 3, 2008.

FIELD OF THE INVENTION

The present invention relates to an indicating device for use with medical injection devices for administering a drug into the body of a subject user wherein the indicating device is configured for visually or tactilely indicating after administration that a dose of the drug actually has been administered and for maintaining this indication until lapse of a pre-defined time interval.

BACKGROUND OF THE INVENTION

Some medication, such as insulin, is typically self-administered using a medical delivery device such as an injection pen. The typical diabetes patient will require injections of insulin several times during the course of a week or a day. However, typical injection devices do not address the problem of a user not remembering when the last injection was administered.

Even shortly after administering a dose of insulin, the user now and then will be in doubt as to whether he actually carried out an injection or not. This could be after minutes or even hours after the intended time for performing an administration. Thus, there exist the potential hazard that the patient chooses not to take his medication or that he takes it twice.

Some prior art devices, such as the electronic syringe disclosed in WO 97/30742, are provided with an electronic monitoring system adapted to automatically start an electronic timer when a selected dose is injected and to show the progress in time on an electronic display. Such an injection device generally provides a satisfactorily solution to the problem addressed above. However, for simpler devices such as disposable injection devices, i.e. the so-called pre-filled devices, the solution with integrated electronics will in most cases not be economically viable. In addition, such a solution may not be environmentally acceptable due to the potential increase in the disposal of electronic components such as batteries etc.

WO 99/43283 include disclosure of a timer device which is intended to be used with pre-filled injection pens, where the timer device is configured for releasable attachment to the pre-filled pen so that the timer device can be removed from a pen once it is ready for disposal and be attached to a new pen. The timer device is configured to detect when an injection is performed and to communicate this via indicator lights that remains turned on for a certain time period from the administration of the dose.

WO 02/064196 includes disclosure of a related timer device, however being more sophisticated in respect of the features it provides.

Although disclosing environmentally acceptable solutions, both the devices of WO 99/43283 and WO 02/64196 offer somewhat complex solutions which require additional operational measures from the user before they can be used. In addition, the device of WO 99/43283 offers a rather bulky design in that it is attached to the rear housing of an injection pen so as to surround it and further requires a second part which couples to the injection button of the device to monitor the movements of the injection button.

In a further reference, U.S. Pat. No. 6,620,133 includes disclosure of a mechanical delay switch equipped injection or infusion device where an acoustical or vibrational signal is emitted when a time delay of 5 to 10 seconds has elapsed after the injection movement has ended to alert the patient to remove the canula from the skin. Further, in U.S. Pat. No. 6,236,624, a mechanical timing device is disclosed which includes a fluid operated timing device which is used for controlling the operation of a further device.

BRIEF DESCRIPTION OF THE INVENTION

Having regard to the above-identified prior art, it is an object of the present invention to provide a timer device solution for medical injection devices which provides a time delay indicator having a visual indication output for signalling the occurrence of a performed injection within lapse of a pre-defined time interval, the timer device being of a less complex construction compared to prior art solutions. A further object is to provide a simple and cost-effective solution so that the time delay indicator will be adaptable for inclusion as an integral part of a pre-filled device and which enables easier operation of the device.

In a first aspect the present invention relates to the use of a time delay indicator in cooperation with a medical injection device of the type having a delivery mechanism including an actuator for the dispensing of drug responsive to user activation of the actuator, the time delay indicator comprises a mechanical time delay device which is started when the actuator is activated and which operates during a pre-defined time interval. The status of the mechanical time delay device is visually and/or tactilely signalized to the user so that the user may readily check whether or not a drug administration has been performed during lapse of the preceding pre-defined time interval.

The time delay indicator may be configured to be in a first visual state prior to activation of the actuator, to be in a second visual state responsive to activation of the actuator, and to be in a third visual state after lapse of a pre-defined time interval measured from the activation of the actuator. The second visual state may be defined as a distinct visual appearance throughout the lapse of the pre-defined time interval or, alternatively, define a gradually changing visual indication. This second visual state should in either case be directly distinguishable by the operator of the device from the first and third visual states.

By incorporating a mechanical time delay device into the time delay indicator, a simple solution is obtained which works in a non-electrical way and hence provides an economically and environmentally acceptable solution. Furthermore, when being built into the medical delivery device as an integral part, a particularly user-friendly solution is provided which do not require any user involvement before use of the timer indicating function.

The time delay indicator may comprise a first part attached to or integral with the actuator and a second part where the first and second parts are adapted to be moveable relatively to each other. In such device, the second part is adapted to be manipulated by the user for causing a visual indicator to change from the first visual state to the second visual state and for starting the operation of the mechanical time delay device.

In particular embodiments, said first and second parts may be further adapted to move relatively during the pre-defined time interval and a visual indication of this state may be controlled by the last mentioned movement. Alternatively, at least one further component of the time delay indicator is released when the mechanical time delay device is started so that the at least one further component moves during the pre-defined time-interval. In such an embodiment the movement of the further component is used for controlling the visual indication of the state of the time delay indicator during lapse of the pre-defined time interval and/or signaling the third visual state, i.e. after lapse of the pre-defined time interval.

In some embodiments, the time delay indicator may be configured so that the second part exclusively moves from the inactivated position towards the activated position when a triggering force acting on the second part exceeds a minimum injection force defined as the minimum force required for activating the actuator. In this way, the triggering of the time delay indicator is prevented when a push-force lower than the minimum injection force is exerted on the actuator. Hence, only operations resulting in a dispensing operation will activate the time delay indicator and thus indicate that an dispensing operation has been performed. As an alternative, or in addition, the activation and operation of the mechanical time delay device does only occur when the relative movement between the first and second mechanical time delay parts exceeds a pre-defined minimum distance.

In particular embodiments, the minimum injection force exceeds 3 N, preferably exceeds 5 N, more preferably exceeds 8 N, more preferably exceeds 10 N, more preferably exceeds 12 N, more preferably exceeds 15 N, and most preferably exceeds 20 N.

In some embodiments, the time delay device further comprises a biasing mechanism adapted to operate the time delay device during lapse of the pre-defined time interval. In some embodiments the biasing mechanism is being pre-strained during actuation of the acutator of the injection device. Alternatively, the biasing mechanism is pre-strained prior to activation of the actuator by an initial action performed by the operator of the device. Still, alternatively, the biasing mechanism may be pre-strained already at delivery of the injection device to the user. The biasing mechanism may comprise a spring, an elastomeric member or a compressible or expandable pneumatic reservoir.

The mechanism for delaying the movement of the second part relative to the first part may comprise a variable sized chamber adapted to contain a flowable medium, the chamber being closed by flow control means for controlling the rate of flow of the flowable medium through the flow control into and/or out of the chamber and wherein the biasing mechanism exerts a force to expand or reduce the chamber. The flowable medium may be air which is being forced out of the chamber during activation of the actuator and which flows back into the chamber during the lapse of the pre-defined time interval or vice versa. The chamber may comprise a check valve which opens during activation of the actuator and which provides a rapid evacuation of air from the chamber. The variable chamber may be provided as a chamber having a slideable piston arranged therein for closing of one end of the chamber.

In alternative embodiments, the time delay indicator may be based upon a configuration having two chambers being in fluid communication via flow control means. The basic configurations shown in U.S. Pat. No. 6,236,624 may be used for constituting the time delay device according to the present invention, this reference being incorporated herein in its entirety.

In other embodiments the time delay device includes a suction cup which adheres to a surface upon activation of the mechanical time delay device and wherein the suction cup adheres to said surface until lapse of said pre-defined interval. Such suction cup mechanism may include a flow control means for gradually allowing air to be sucked into the space confined between the suction cup and the said surface. The suction cup mechanism may further include a biasing means which urges the suction cup away from the said surface. In particular simple embodiments, the suction cup, the biasing means and the flow control means are constituted by one and the same member. Such embodiments may include a unitary member made of a silicone rubber material.

In still other embodiments, the mechanical time delay device is provided as a watch-type timer which is wound up during the injection procedure and which returns to an initial state after lapse of the pre-defined time interval.

In particular embodiments, the pre-defined time interval is longer than 30 minutes, such as longer than 1 hour, such as longer than 2 hours, such as longer than 3 hours, such as longer than 5 hours, such as longer than 24 hours, such as longer than 36 hours.

The time delay element may, according to the first aspect of the invention, be configured so as to re-initialize the timing function if a renewed activation of the actuator occurs during lapse of a previously initiated pre-defined time interval.

In some embodiments the third visual state of the time delay indicator corresponds to the first visual state for the indicating member. In such a system, the time delay indicator returns automatically to the initial state after lapse of the pre-defined time delay. In other embodiments, the third state of the indicating member is different from the first state. In such a system, a user operation may be required for bringing the time delay indicator from the third state into its initial state (the first state).

The visual indicator according to the first aspect of the invention may be provided as one or more of said parts which moves during operation of the time delay indicator so that the position of said parts visually indicates the state of the device. Other embodiments include a visual indicator, the appearance of which is controlled by the position or movements of the movable parts. All types of visual indicators providing a change in a visual property, such as colour, and being controlled by the mechanical time delay mechanisms as disclosed herein may be used in conjunction with the present invention.

The visual indicator of the time delay indicator may be configured to remain in the second visual state after activation of the actuator and until lapse of the pre-defined time interval whereafter the indicating member returns to the first visual state. In such an embodiment, the visual indicator may be of the on-off type having only two distinct visual indications.

In other embodiments, the visual indicator is configured to gradually change state after activation of the actuator and until lapse of the pre-defined time interval so as to provide a measure of elapsed time since activation of the actuator. Such gradually state change may be accomplished as a continuous or step-wise change.

The medical delivery device may for example be in the form of an injection pen, either of the durable type where a medicine filled reservoir or cartridge is removably attached or of the pre-filled type where a medicine filled reservoir or cartridge is irremovably arranged in the pen. Alternatively, instead of a pen, the medical delivery device may be in the form of a doser. The medical delivery device may be of the manual type, where a user, during injection, supplies the force necessary for expelling medicine from the reservoir. Alternatively, the medical delivery device may be of the kind commonly known as a wind-up pen or AutoPen®, e.g. an injection device where the user, during an initial procedure, delivers the mechanical energy required for the expelling operation, the mechanical energy being stored as potential energy for example in a spring member.

In embodiments where the time delay indicator is adapted to removably attach to the medical injection device, such removable attachment may be provided as a mechanical coupling to the actuator of the injection device. Suitable attachments may be provided as a snap-coupling, a threaded coupling or a bayonet coupling. Other removable attachments may be provided by adhering such as by glueing or by using fasteners such as Velcro™-type fasteners.

In a still further embodiment, the time delay indicator attaches non-removably to the medical delivery device so as to form one unitary disposable assembly. In such systems the time delay indicator may be made distinct from the actuator or the indicator may be made as an integral part of the actuator, e.g. so as to constitute the actuator.

In a second aspect, the invention relates to a medical delivery device for introducing a drug into the body of a subject user, the delivery device comprising: (a) a delivery mechanism including an actuator for the dispensing of drug responsive to user activation of the actuator, and (b) a time delay assembly comprising a first part which couples to the actuator of the medical delivery device, and a second part which moves in response to a push-force acting on the second member to activate the actuator, wherein said movement activates the time delay assembly and wherein the second member exclusively moves from the inactivated position towards the activated position when the push-force acting on the second member exceeds a minimum injection force defined as the minimum force required for activating the actuator.

In the context of the present invention, the term "medical injection device" shall be understood as any device capable of actively bringing a medicament-containing drug into the body of a user by means of an appropriate delivery mechanism such as by using a canula or by a needle-less jet-stream. A non-exhaustive list of medical injection devices within the context of the present invention comprises pre-filled or durable injectors such as pen-shaped injectors or dosers. The drug may be flowable or solid such as drugs forming medicine pegs for insertion through the derma. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

DETAILED DESCRIPTION OF THE INVENTION

The invention will now be described in further detail with reference to the drawings in which.

Figure 1:
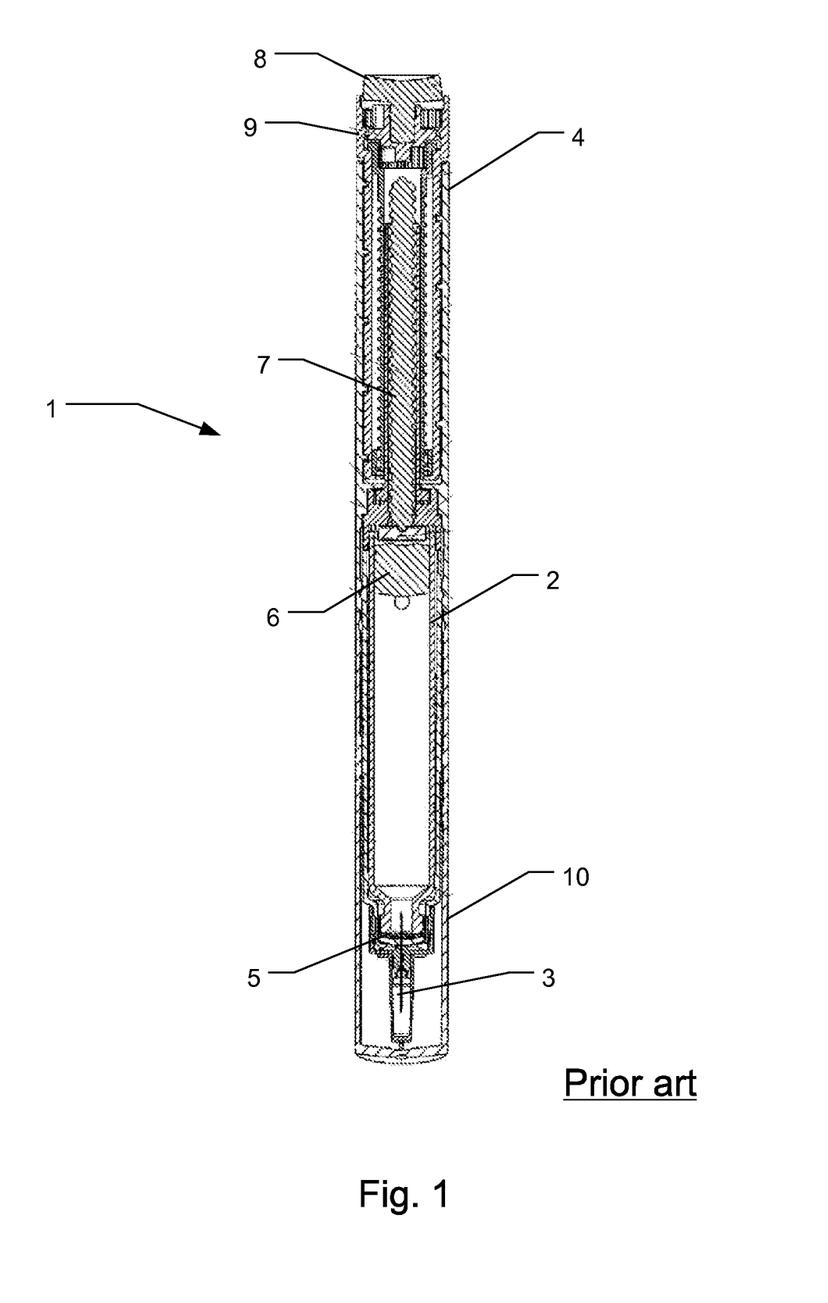
FIG. 1 shows a prior art medical injection device.

FIG. 1 discloses a prior art medical injection system forming an injection pen 1 comprising a medicament filled cartridge 2 which is accommodated in a distal part of the pen. The proximal part 4 of the device holds a mechanism for setting and injecting specific doses of a medicament from the cartridge 2. The cartridge 2 comprises a passage in a distal neck part which is sealed by a piercable sealing member 5. Cartridge 2 further comprises a slideably mounted piston 6 which is adapted to slide towards the distal part of the container 2 when a force is exerted on the piston 6 in the distal direction. Typically, medication is delivered through a needle canula 3 which may be releasably secured to the distal part of the pen. The injection pen further comprises an actuator which may be manipulated by the hand of the user for selecting a dosage and for injecting the set dosage. In the depicted form, the actuator comprises a dose dial 9 which is turned for setting the dose size and an injection button 8 which is pressed forward in the distal direction to inject the set dosage. A distally directed force on the button 8 exerted by the hand of the user is transferred by the dosing mechanism 7 of the pen to the piston 6 of cartridge 2. The distal part of the device further shows a cap which protects the cartridge and the needle when the device is stored.

Figure 2:
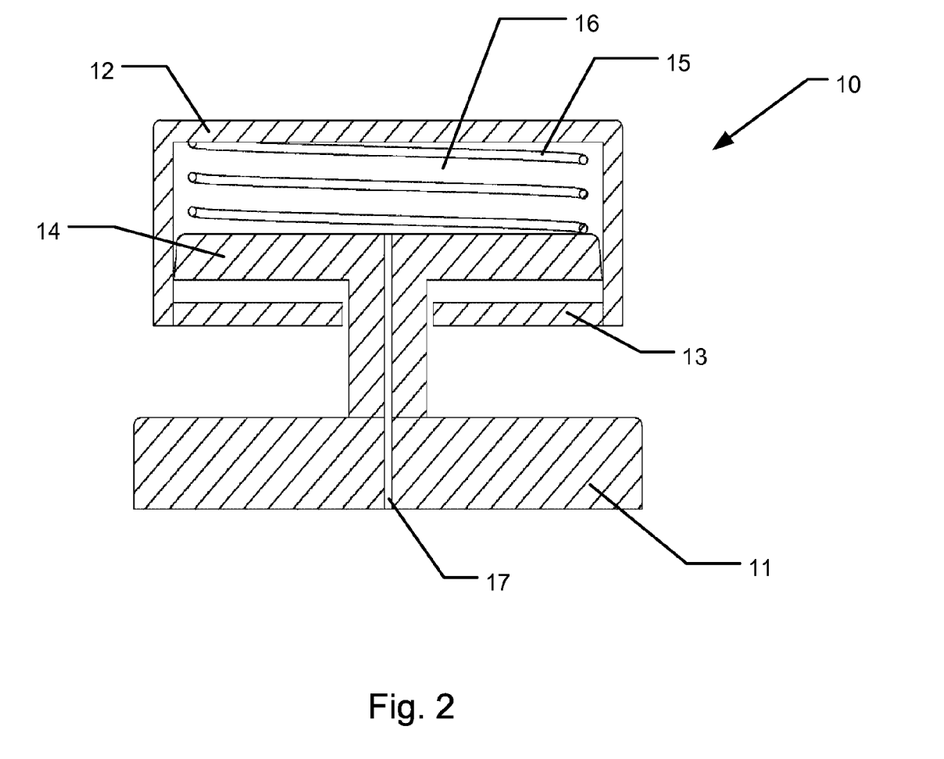
FIG. 2 is a schematic cross-sectional representation of a first embodiment of the invention showing a mechanical time delay indicator.

FIG. 2 shows a cross-sectional schematic representation of a first embodiment of a time delay indicator 10 according to the invention. In the depicted form, the time delay indicator is intended to be an integral part of an injection pen such as the one shown in FIG. 1. In FIG. 2, the time delay indicator forms part of an actuator which comprises a first part 11 that connects to the dosing mechanism of the device and a second member 12 that performs as a button of the actuator for injecting either a set dose or a fixed dose. The second member 12 is slideably mounted with respect to the first member 11 so that he slideable movement is parallel with an axis which forms the centre axis of the injection pen.

The proximal part of the first member 11 forms a piston 14 which is arranged in a distally facing cavity of the second member 12. The walls of the second member 12 and the piston 14 forms a variable volume chamber 16 where the cooperating faces of the walls and the piston 14 forms an air-tight coupling. An opening formed in the distal part of the first member 11 forms an air flow controller 17 for controlling flow of air from the chamber to ambient air and is so dimensioned that a controlled flow rate of air is allowed to pass through the air flow controller 17 when the second member 12 slides relatively to the piston 14. Accommodated in chamber 16 is a spring member 15 which biases the second member 12 in the proximal direction away from the first member 11. Distally arranged wall sections of the second member 12 forms a retention section 13 so as to retain the second member 12 in the most proximal position when no external force is exerted on second member 12. In addition, the retention section 13 defines the amount of travel that the second member is allowed to move when it is moved in the distal direction, i.e. when a sufficient force acts in the distal direction upon the second member 12 for performing an injection.

In the state shown, no force acts upon the second member 12, hence the second member 12 rests in its most proximal direction, i.e. an inactivated position. When a user attempts to inject a set dose, a proximally directed force moves the second member 12 in the distal direction while the spring member is compressed. However, spring member 15 is so dimensioned that no or substantially no movement occur if the external force acting on the second member 12 is below the required force for expelling medication from the cartridge.

The time delay indicator 10 may include a check valve (not shown) which allows rapid evacuation of air from chamber 16 during the injection procedure. The second member 12 continues to move relative to the first member 11 until the distal face of the retention section 13 hits a proximal arranged face of the first member 11. The second member 12 maintains this position, i.e. an activated position, as long as the user continues to inject medication.

Upon release of the external force, the spring member 15 expands to its initial length, during which air is re-introduced to the chamber 17 through the air flow controller 17. The air-flow resistance of air flow controller 17 and the spring constant of spring member 15 determine the rate of return of air, and thereby the return movement of second member 12 relative to first member 11. Thus, the movement constitutes a timer function where the return movement to the initial inactivated position, or alternatively to a different end-position, ends at a pre-defined time delay after activation. The position of the second member 12 with respect to first member 11 may be used as an indicator for progress of the time delay function. To increase the intelligibility of the indicator, the narrow part of the first member 11 may be provided with a marking, either as a single distinct marking for signalling expiry of the pre-defined time delay or as a scale marking, e.g. by marking partial or full hours passed since activation.

In alternative embodiments, the second member 12 may be made of transparent material so that at least a part of the first member 11 is visible through the transparent material which then is visible for reference. The position of the second member 12 is used to visually indicate the state of the injection device, i.e. whether the device is in a state where an injection has been performed within the pre-determined time interval or in a state where injection has not been performed within the pre-determined time interval. It will be appreciated, that in addition to a visual indication, a tactile indication may be provided by allowing the relative position of the first member 11 and the second member 12 to be examined tactilely.

The air flow controller 17 may in particular embodiments contain a thin membrane which allows air to slowly migrate through the membrane during the predetermined time interval. Such membrane based air flow controller will be further described in accordance with FIGS. 3a-3d below.

FIGS. 3a through 3d schematically depicts a second embodiment of a time delay indicator 20 according to the invention, each of the four drawings showing a respective one of four different states of time delay indicator 20.

Figure 3A:
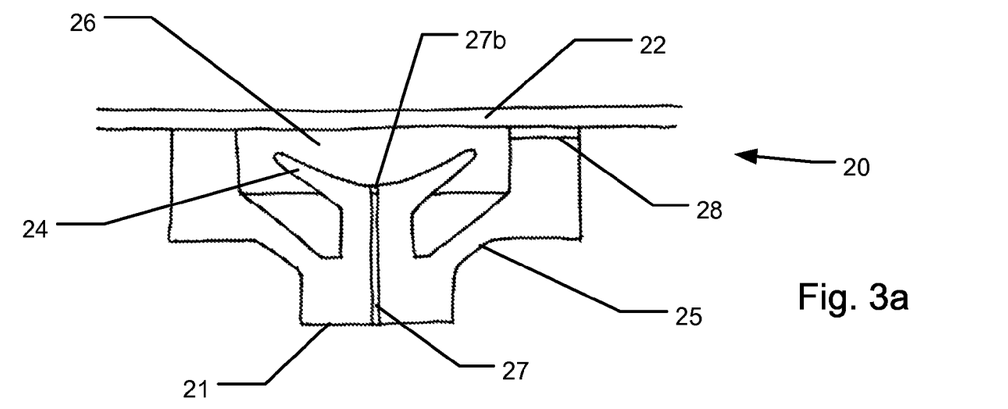
FIG. 3a-3d show schematic cross-sectional representations of different states of a mechanical time delay indicator of a second embodiment according to the present invention, FIG. 4 show an embodiment of a time delay assembly according to the second aspect of the invention mounted on the injection button of an injection device, and FIG. 5 show a simple electronic circuit for inclusion in the embodiment shown on FIG. 4.

In FIG. 3a the time delay indicator 20 again represents a part of an actuator which may be used in conjunction with a medical injection device such as the one shown in FIG. 1. The time delay indicator 20 is intended to substitute the actuator 8 of FIG. 1 and includes a first member 21 and a second member 22. The second member 22 performs as a button for actuating injection of a previously set dose or alternatively injection of a fixed dose. The second member 22 is generally cylindrical having an open interior adapted to accommodate the first member 21. However, in the drawings, only a section of the extreme proximal wall section of second member 22 is visible. The first member 21 interconnects between the second member 22 and the dosing mechanism of the injection device so that the second member 22 is able to slide axially a small distance with respect to a connecting part of the dosing mechanism.

The first member 21 is in the shown embodiment formed as a unitary part of a resilient material which deforms when subject to pressure. The first member comprises a proximal ring shaped outer section which along its periphery is attached to a distally facing wall of the second member 21. A conical section 25 bridges the proximal ring shaped section with a distal central part. The distal central part of first member 21 is attached to a connecting part of the dosing mechanism of the injection device. The proximal ring shaped section, the conical section 25 and the distal central part forms a chamber 26 which is closed off by the second member 22.

Inside chamber 26, a suction cup 24 is formed which extends into the chamber 26 from the distal central part of first member 21. Suction cup 24 is arranged to face the distal face of the proximal wall section of second member 22. Due to the resiliency of first member 21, and in particular due to conical section 25, the second member 22 and the proximal ring section of the first member 21 is configured to be slightly movable with respect to the distal central part of first member 21.

A small channel 28 is arranged so that air inside chamber 26 may evacuate rapidly away from chamber 26. Hence, when a force is exerted on the second member towards the distal end of the device, the proximal wall section of second member 22 approaches and touches suction cup 24. As suction cup 24 forms an annular sealing lip against second member 22 the suction cup 24 will obtain an adherence towards second member 22.

Figure 3B:
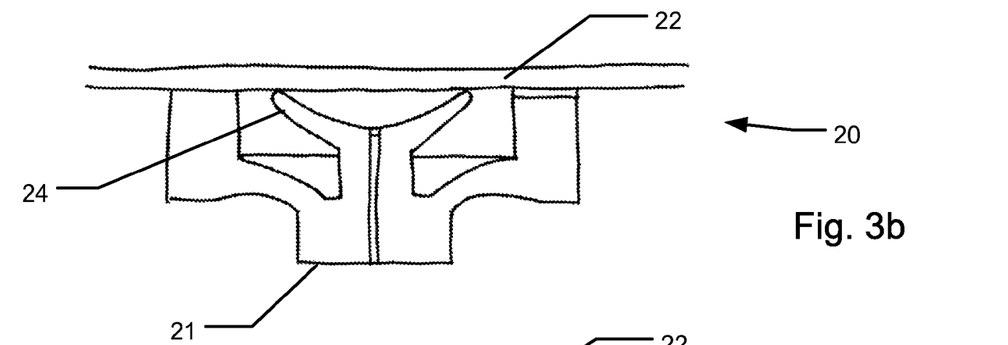
Figure 3C:
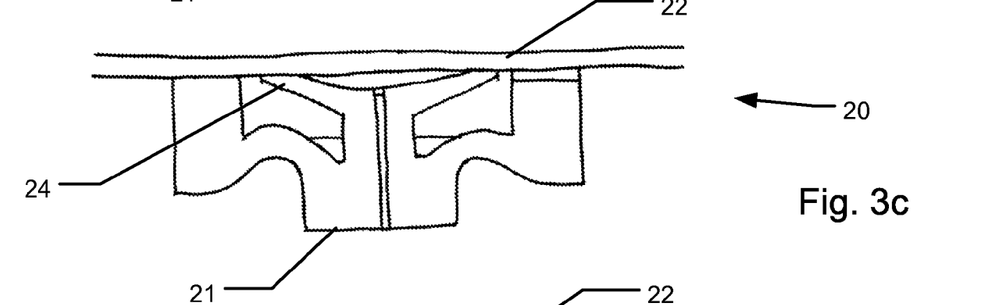

Before an injection has been performed and when no external force is exerted upon second member 22, the time delay indicator 20 will remain in the state shown in FIG. 3a. However, when axial force is exerted in the distal direction, the time delay indicator will gradually change state in dependence of the amount of axial force exerted until the state shown in FIG. 3d has been obtained. FIG. 3b shows the state where the second member 22 has initially made contact with the suction cup 24 and FIG. 3c shows an intermediate state where a small amount of air within the suction cup 24 has escaped from its annular sealing lip so that the suction cup 24 has obtained adherence to some degree towards the second member 22.

The first member 21 may be formed by an elastomeric material such as silicone rubber. An appropriate silicone rubber may be used having a Shore A hardness of around 45-55. The proximal wall section of the second member 22 is preferably transparent and may be made of glass, PC or PMMA or similar material having the required surface finish to obtain long-time adherence of suction cup 24.

As shown in FIG. 3a a channel 27 is formed in the central part of the first member 21 so as to allow controlled passage of ambient air to the central part of the suction cup 24. A thin membrane 27b covers the opening of the passage 27 and acts as an air flow controller by allowing air to be slowly sucked into the space between the suction cup 24 and the second member 22 once adherence of the suction cup has been obtained and the external force exerted upon second member 22 has been released. The membrane 27b is in the shown embodiment formed of silicone rubber having a thickness of about 1/10 mm. As air will slowly dissipate through the thin membrane 27b the adherence of suction cup 24 towards the second member 22 will gradually reduce.

In the shown embodiment the channel 27 is formed in the central part of first member 21 and emerges centrally on suction cup 24. The thin membrane 27b is arranged where the channel 27 emerges within the suction cup space. However, the channel 27 as well as the membrane 27b may be arranged differently on or within the suction cup 24. Also, instead of forming an air passage in the suction cup 24, a similar air passage may be arranged in second member 22. Alternatives to the air dissipating membrane 27b will also be readily acknowledged by the skilled worker.

The resiliency of the first member 21 acts to return the configuration of time delay indicator 20 towards its initial state as shown in FIG. 3a. Hence, when pressure has been released from the actuator of the device, the second member 22 will be gradually moved away from the state shown in FIG. 3d towards the state shown in FIG. 3a. Although not shown, this state change will basically follow the reverse order of FIGS. 3a-3d although slightly different due to the forces exerted on the resilient member 21 differing slightly during the injection procedure from the forces exerted during the return movement.

The state of the time delay indicator may be visually inspected by checking the position of the second member 22 relative to the first member 21, e.g. by checking whether or not the actuator button (second member 22) has been fully pressed in relative to the housing part of the device. It is noted that due to the resiliency of the first member 21, the actuator button (second member 22) will be pushed slightly away from the housing of the injection device during or at the end of the pre-defined time interval. It will be appreciated that such embodiment also will provide a tactile indication of the state of the time delay indicator 20. In embodiments where the second member 22 include a transparent section, the position of the distal part of the first member 21 relative to the second member 22 may be checked visually. In embodiments where the proximal wall section of second member 22 is made transparent, the parts of second member 22 to which the suction cup 24 adheres will appear darker than the remaining part of second member 22 providing a colour indication as to whether an injection has been performed or not within the past pre-defined time interval. In addition, other visual indicators providing a change in a visual property such as colour and being controlled by the mechanical time delay mechanisms as disclosed herein may be used in conjunction with the present invention.

It will be appreciated that the time delay indicator 20 may be designed so that a minimum force and/or a minimum stroke length will be necessary before activation and operation of the time delay indicator is obtained. This will ensure that the time delay indicator 20 will only be activated when a regular injection is performed while not being activated by error.

Figure 3D:
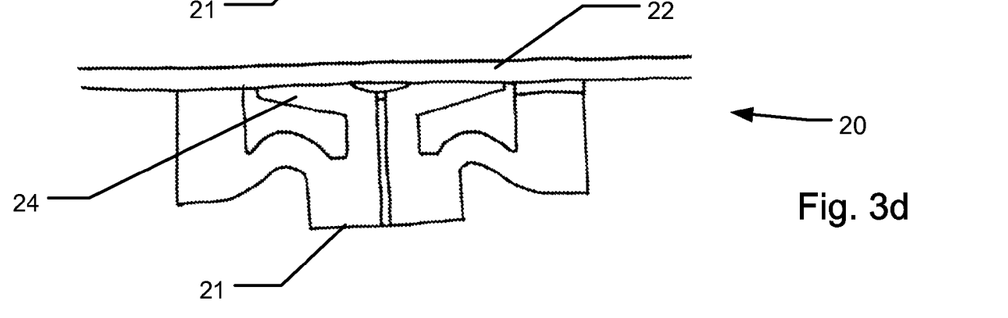

It will be appreciated that the return movement from the state shown in FIG. 3d to the state shown in FIG. 3b occur very slowly, e.g. within a number of partial or full hours, whereas the return movement from the state change shown in FIG. 3b to the initial state shown in FIG. 3a occur rapidly. The actual geometrical design of the resilient first member 21 as well as the selection of the materials and the air flow controller may be chosen such as to adapt the pre-defined return time interval of the time delay indicator to the particular medication administration scheme in question. For example, when the injection device should be used for administrations 3 times pr. day, the pre-defined time interval of the time delay indicator may be chosen in the order of say ½ to 5 hours. For once daily injections, the pre-defined time interval may be chosen in the order of say 10 to 15 hours and for once weekly injections, the pre-defined time interval may be chosen in the order of say 24 to 36 hours.

While the embodiment of the time delay indicator 20 as shown in FIGS. 3a-3d has been shown as a two member assembly where the two members move relatively during lapse of the pre-defined time interval, other embodiments may incorporate other configurations having more or less elements. For example, a unitary embodiment may be obtained by using a suction cup element similar to first member 21 of time delay indicator 20, where the suction cup is arranged to engage and adhere to a part of the dosing mechanism and where the user pushes directly on a part of the time delay indicator "behind" the suction cup. Hence, in such an embodiment, the position of the suction cup, i.e. whether it adheres to the dosing mechanism or not, is taken as an indication as to whether or not an injection has been performed within the past pre-defined time interval.

Figure 4:
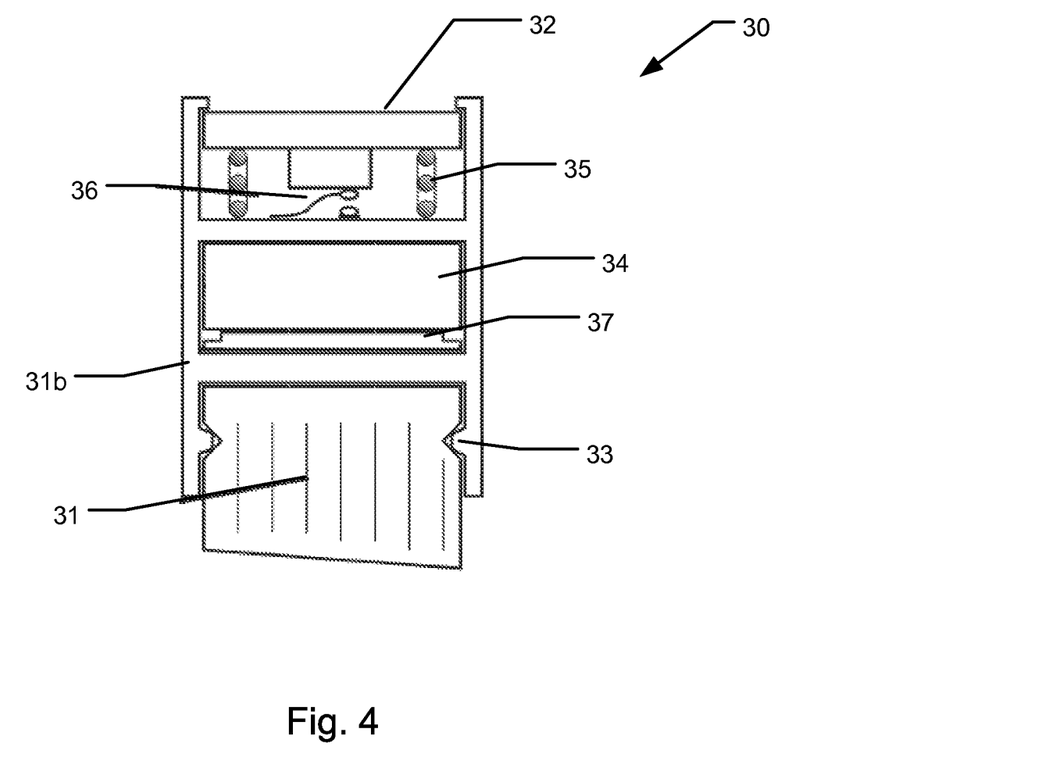

FIG. 4 discloses an embodiment according to a second aspect of the invention. An electronic time delay assembly 30 having an external housing 31b is to be put on an injection pen's dosing button 31 and fixated e.g. by a snap lock 33. The top part of the time delay assembly consist of a reinforced display 32 also functioning as a push-button for the user transferring the push force to the injection pen's dosing button 31. The display 32 is mounted on e.g. a flex pcb (not shown) so that the display 32 is movably mounted with respect to the housing 31b in a distal direction in response to the push-force exerted by the user. Furthermore, inside housing 31b, a microprocessor unit 34, a battery 37 and a mechanical switch 36 is mounted.

Between the display 32 and the housing 31b a spring member 35 is placed. When the force (by the user's finger) on the display part 32 surpass a certain preset spring force created by the spring member 35, the switch 36 will be closed indicating a dosing takes place and a continued and increased force on the display part will be transferred to the injection pen's dosing button 31 and a dosing takes place. A timer function in the microprocessor 34 starts and a dosing display is shown on the time delay assembly's display 32. The timer counts time against a preset time and the time duration since dosing detected by the switch 36 is shown in the display 32 e.g. by a count down appearance. When the preset time is reached the displays appearance is as it was before the dosing was initiated.

Figure 5:
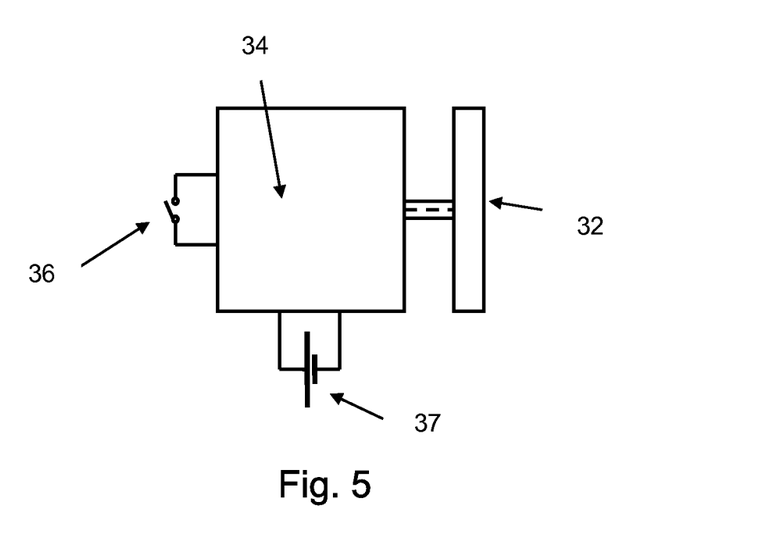

FIG. 5 shows a schematic representation of the electronic circuit comprised in a time delay assembly 30. The switch 36 constitutes together with the spring member 35 detection means for the dosing taking place and an algorithm in the software starts the displaying in the display 32 as well as starts the timer (here an internal part of the microprocessor 34). The switch can also start-up the microprocessor 34 from a deep-sleep mode saving power and energy from the battery 37 when no dosing or displaying takes place and after displaying the microprocessor can be put down into deep-sleep again.

Some preferred embodiments have been shown in the foregoing, but it should be stressed that the invention is not limited to these, but may be embodied in other ways within the subject matter defined in the following claims. The figures e.g. discloses medical delivery systems of the present invention in the form of an injection pen, however, this particular delivery device and its shape is in no way limiting for the present invention as defined in the claims. This also applies to time delay indicators being more fully integrated into an injection device than the embodiments shown in this disclosure, e.g. time delay indicators being integrated into a dosing mechanism such as providing an indicator viewable through a window of a housing of the device or alongside a dose amount indicator such as a dose dial scale. Also, actuators for activating an injection other than the push-button type described in the application are within the subject matter defined in the following claims. A non-limiting example being devices having and actuator which is automatically activated subject to insertion of a needle into the skin of a subject user. Furthermore, additional intermediate visual status indications may be provided between the said first, second and third visual states without departing from the scope of the subject matter defined in the claims.

The invention claimed is:

1. A medical injection pen for introducing a drug into the body of a subject user, the medical injection pen comprising:
   a medicament filled cartridge comprising a piercable sealing member and a slidably mounted piston,
   a delivery mechanism including an actuator for the dispensing of drug responsive to activation of the actuator, and
   a time delay indicator adapted to change from a first visual state prior to activation of the actuator to a second visual state responsive to activation of the actuator, and to change to a third visual state after lapse of a pre-defined time interval subsequent to activation of the actuator,
   wherein the time delay indicator comprises a mechanical time delay device which is started responsive to activation of the actuator and which operates until lapse of said pre-defined time interval, the visual state of the time delay indicator being controlled by the mechanical time delay device,
      wherein the mechanical time delay device comprises;
         a first part attached to or integral with the actuator of the delivery mechanism,
         a second part, the second part being relatively moveable with respect to the first mechanical time delay part, wherein the second part is adapted to be manipulated by the operator from an inactivated position into an activated position for activating the mechanical time delay device and the actuator for causing the time delay indicator to change from the first visual state to the second visual state,
      wherein the pre-defined time delay is longer than 30 minutes,
      wherein the first part and the second part are adapted to move continuously or intermittently relative to each other during lapse of said pre-defined time interval,
      wherein a variable sized chamber adapted to contain a flowable medium is coupled between the first part and the second part, the variable sized chamber being closed by a flow control structure for controlling the rate of flow of the flowable medium through the flow control structure into and/or out of the variable sized chamber, and
      wherein a biasing mechanism is adapted to operate the time delay device during lapse of a pre-defined time interval by exerting a force to expand or reduce the variable sized chamber.

2. A medical injection pen as defined in claim 1, wherein the time delay indicator comprises a visual indicator coupled mechanically or integrated into one of said first part and second part and wherein the visual status of the visual indicator is adapted to change upon movement of one or more of said first part and second part.

3. A medical injection pen as defined in claim 1, wherein the time delay device is configured so that it is exclusively activated when a triggering force acting on the second part exceeds a minimum injection force defined as the minimum force required for activating the actuator and/or when the relative movement between the first part and second part exceeds a pre-defined minimum distance.

4. A medical injection pen as defined in claim 1, wherein the biasing mechanism is selected from the group consisting of a spring, an elastomeric member and a compressible or expandable pneumatic reservoir.

5. A medical injection pen as defined in claim 1, wherein the third visual state corresponds to the first visual state.

6. A medical injection pen as defined in claim 1, wherein the time delay indicator is configured to continuously or intermittently change state after activation of the actuator and until lapse of the pre-defined time interval so as to provide a measure of elapsed time since activation of the actuator.

7. A medical injection pen as defined in claim 1, wherein the variable sized chamber comprises a check valve which opens during activation of the actuator.

8. A medical injection pen as defined in claim 1, wherein the pre-defined time delay is longer than 1 hour.

9. A medical injection pen as defined in claim 8, wherein the pre-defined time delay is longer than 2 hours.

10. A medical injection pen as defined in claim 9, wherein the pre-defined time delay is longer than 3 hours.

11. A medical injection pen as defined in claim 10, wherein the pre-defined time delay is longer than 5 hours.

12. A medical injection pen as defined in claim 11, wherein the pre-defined time delay is longer than 24 hours.

13. A medical injection pen as defined in claim 12, wherein the pre-defined time delay is longer than 36 hours.

* * * * *